United States Patent [19]

Dukes

[11] Patent Number: 5,042,498
[45] Date of Patent: Aug. 27, 1991

[54] INTELLIGENT ELECTROCARDIOGRAM SYSTEM

[75] Inventor: John N. Dukes, Los Altos Hills, Calif.

[73] Assignee: Hewlett-Packard Company, Palo Alto, Calif.

[21] Appl. No.: 505,795

[22] Filed: Apr. 6, 1990

[51] Int. Cl.$^5$ .............................................. A61B 5/04
[52] U.S. Cl. .................................. 128/696; 128/640; 128/641
[58] Field of Search ................ 128/696, 639, 640, 641

[56] References Cited

U.S. PATENT DOCUMENTS

| | | | |
|---|---|---|---|
| 3,495,584 | 2/1970 | Schwalm | 128/696 |
| 3,602,215 | 8/1971 | Parnell | 128/696 |
| 3,757,778 | 9/1973 | Graham | 128/696 |
| 3,834,373 | 9/1974 | Sato | 128/640 |
| 4,235,241 | 11/1980 | Tabuchi et al. | 128/639 |
| 4,598,281 | 7/1986 | Maas | 128/696 |

*Primary Examiner*—Francis Jaworski
*Assistant Examiner*—George Manuel

[57] ABSTRACT

An Intelligent Electrocardiogram System that solves the problem of faulty electrical connections between a patient and an ECG instrument is disclosed. The electrode employed by the invention comprises a disposable insulative pad and a snap connector that includes an LED anchored in the top central portion of the snap connector. Wires from the LED run into a lead that extend to an ECG instrument. An adhesive attached to the pad enables the electrode to be secured on the skin of a patient. The electrode includes a metal post embedded in the center of pad. The post protrudes up from the insulative pad through the connector side, which is the side opposite the side that touches the patient's skin. A spring contact surrounds the post and provides an electrical coupling to one of the wires inside the lead. The bottom portion of the post extends through and past a lower central surface of the pad that is capable of holding a volume of conductive jelly. A sensor circuit connected to the spring clip includes a current source, a comparator, and a current limiting resistor. A reference voltage Vr is applied to the comparator's negative input, while the positive is linked to the spring contact. The output of the comparator flows through a resistor that is coupled to the LED. When a change in the impedance between the conductive portion of the electrode and the patient is detected, the sensor circuit activates the LED on the faulty electrode.

9 Claims, 7 Drawing Sheets

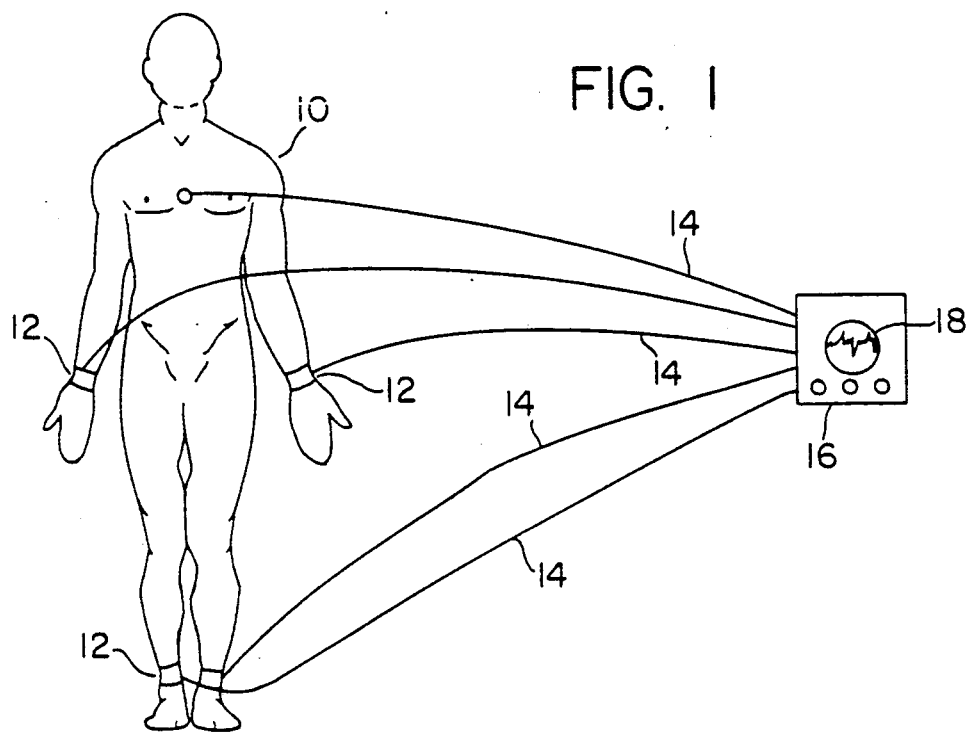
FIG. 1
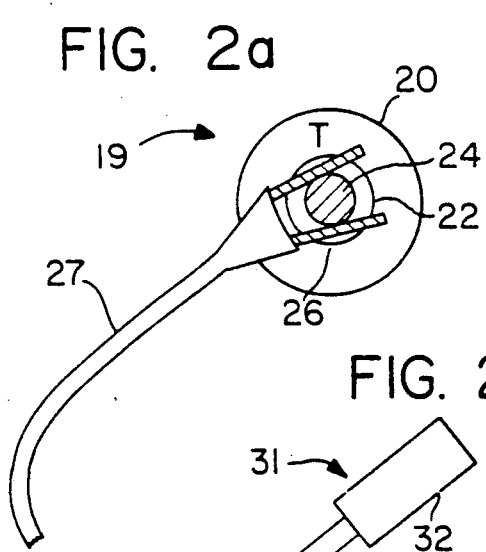
FIG. 2a
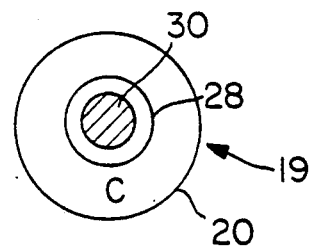
FIG. 2b
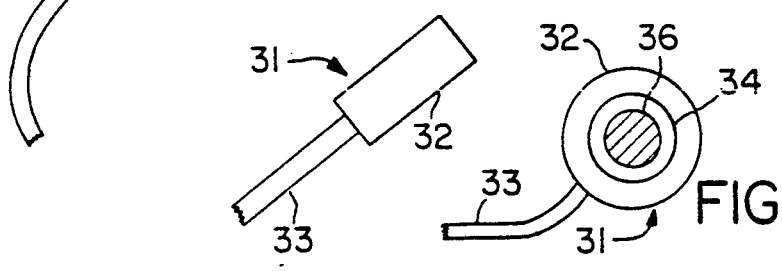
FIG. 2c
FIG. 2d 5,042,498

INTELLIGENT ELECTROCARDIOGRAM SYSTEM

BACKGROUND OF THE INVENTION

The present invention is a method and apparatus that provides an electrocardiographic system that detects faulty electrode attachments and guides a technician to insure that leads to the patient are connected in the proper order and in the correct position on the patient's skin.

An electrocardiogram (ECG) is a printed graph of the waveform generated by the cyclical activation of the heart. The ECG is a measurement of potential difference that requires at least two electrodes to be placed on a patient's skin. Conventional systems employ adhesive discs or pads having a conductive inner section that is applied directly to the patient's chest. This adhesive section is coupled to a terminal on the opposite side of the disc that faces away from the skin. A wire lead is clipped to this terminal which conveys the electrical signal to the ECG instrument.

The quality of the ECG measurement depends almost entirely upon a good connection between the patient's skin and the adhesive pad. Since ECG tests are often performed while the patient is on a moving treadmill to induce increased heart and respiratory rates, one common problem encountered by technicians performing this medical examination is an inadequate connection between the pads and the skin. This problem is especially troublesome during complex procedures involving the application of many adhesive discs. Recent advances in cardiac medicine have enabled physicians to make more accurate diagnoses of serious heart conditions. These advanced techniques involve ECG tests that require the placement of fifty or more electrodes on the person being tested. One pad among fifty that is poorly coupled to the epidermis can be difficult to isolate and may even ruin one of these complex examinations.

The problem of providing a highly reliable ECG device has presented a major challenge to designers in the health care field. The development of a straightforward method of insuring good electrical connections to the patient during an ECG examination would represent a major technological advance in the instrumentation business. The enhanced performance which could be achieved using such an innovative device would satisfy a long felt need within the medical profession.

SUMMARY OF THE INVENTION

The Intelligent Electrocardiogram System is a method and apparatus that solves the problem of faulty electrical connections between a patient and an ECG instrument. The present invention senses a faulty or inadequate electrical coupling between the ECG electrode and the patient's skin. When a change in the impedance between the conductive portion of the electrode and the patient is detected, a visual warning is issued by a light emitting diode (LED) affixed on the electrode. This signal informs the technician performing the ECG examination to correct the failed coupling to the patient. The LED may be replaced or accompanied by an audible warning. The Intelligent Electrocardiogram System may also be used in conjunction with an electrocardiogram instrument that includes a microprocessor and memory to guide a technician to connect the many leads on the patient to the instrument in the proper sequence and to the proper locations.

An appreciation of other aims and objectives of the present invention and a more complete and comprehensive understanding of this invention may be achieved by studying the following description of a preferred embodiment and by referring to the accompanying drawings.

BRIEF DESCRIPTION OF THE DRAWINGS

FIG. 1 is a schematic representation of a patient connected to a conventional electrocardiograph instrument.

FIGS. 2(a, b, c, and d) are perspective views of conventional ECG electrode hardware.

DETAILED DESCRIPTION OF A PREFERRED EMBODIMENT

Figure 3:
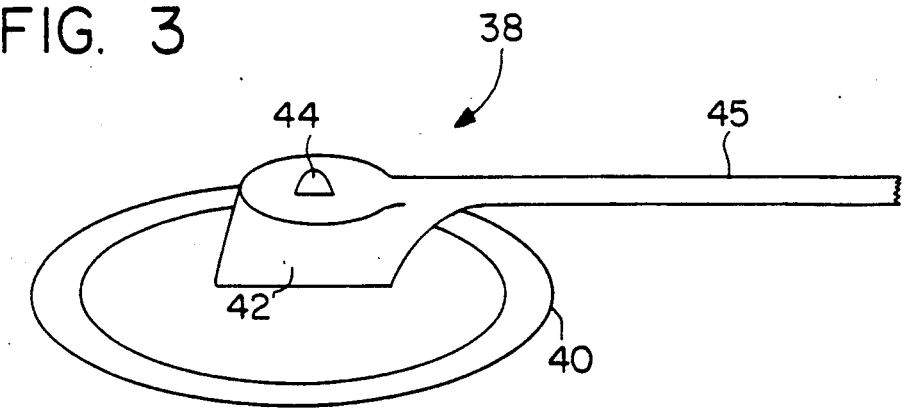
FIG. 3 is a perspective view of the preferred embodiment of the electrode employed by the Intelligent ECG System.

FIG. 1 depicts a patient 10 who is being monitored by a conventional electrocardiograph instrument. Electrodes 12 borne by bands or pads are attached to the patient's skin. These electrodes 12 are coupled to a set of leads 14 which provide input signals to an ECG instrument 16 that generates cardiovascular waveforms on display 18. Conventional ECG electrode hardware is portrayed in FIG. 2. A typical previous electrode 19 as shown in FIGS. 2(a) and 2(b) includes a terminal side "T" and a contact side labeled "C". The electrode 19 has outer and central portions 20 and 22 and a terminal 24 which receives a spring clip 26 that is connected to a lead 27. The obverse or contact side C of the same electrode 19 is portrayed in FIG. 2(b), which reveals an outer portion 20, an inner portion 28 and a central conductive portion 30. A snap connector 31 may be used in place of the spring clip 26. FIG. 2(c) is a side view of this conventional snap connector 31 that includes an outer portion 32 and a lead 33. FIG. 2(d) is a bottom view that illustrates outer portion 32, and a conductive portion 34 that forms a recess 36 in the center of snap connector 31.

Figure 4:
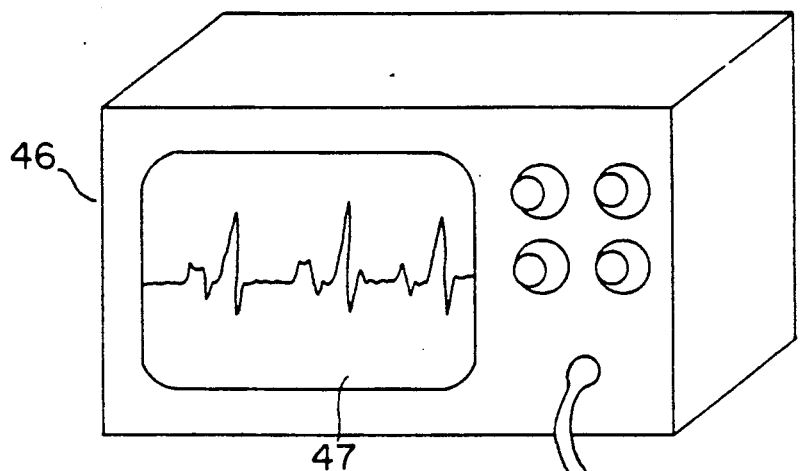
FIG. 4 is a perspective schematic depiction of the Intelligent ECG System.
Figure 4:
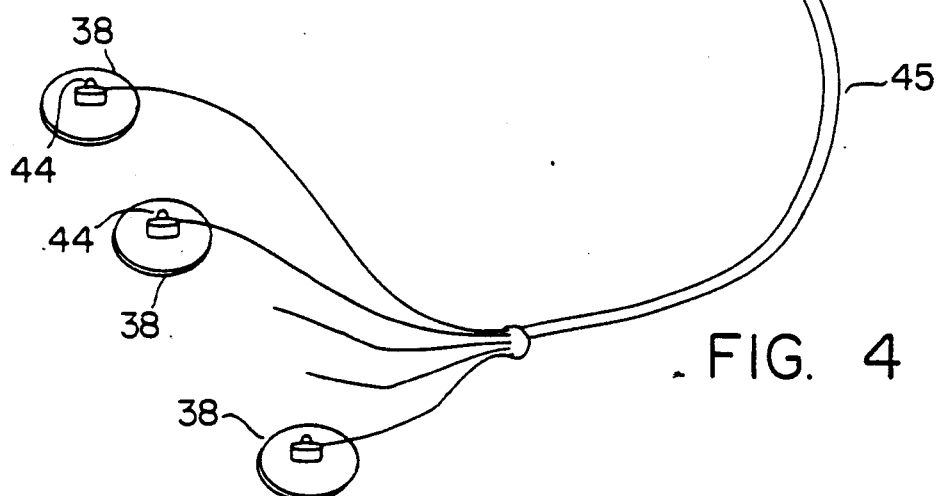

FIG. 3 is a schematic perspective view of the electrode 38 employed by the preferred embodiment of the Intelligent ECG System. An electrode 40 having a contact side 40a and a connector side 40b is coupled to a snap connector 42 that includes a light-emitting diode (LED) 44 and a lead 45. FIG. 4 is a perspective schematic depiction of the Intelligent ECG System comprising several electrodes 38 with LEDs 44 linked by leads 45 to an ECG instrument 46 that includes a display 47.

Figure 5:
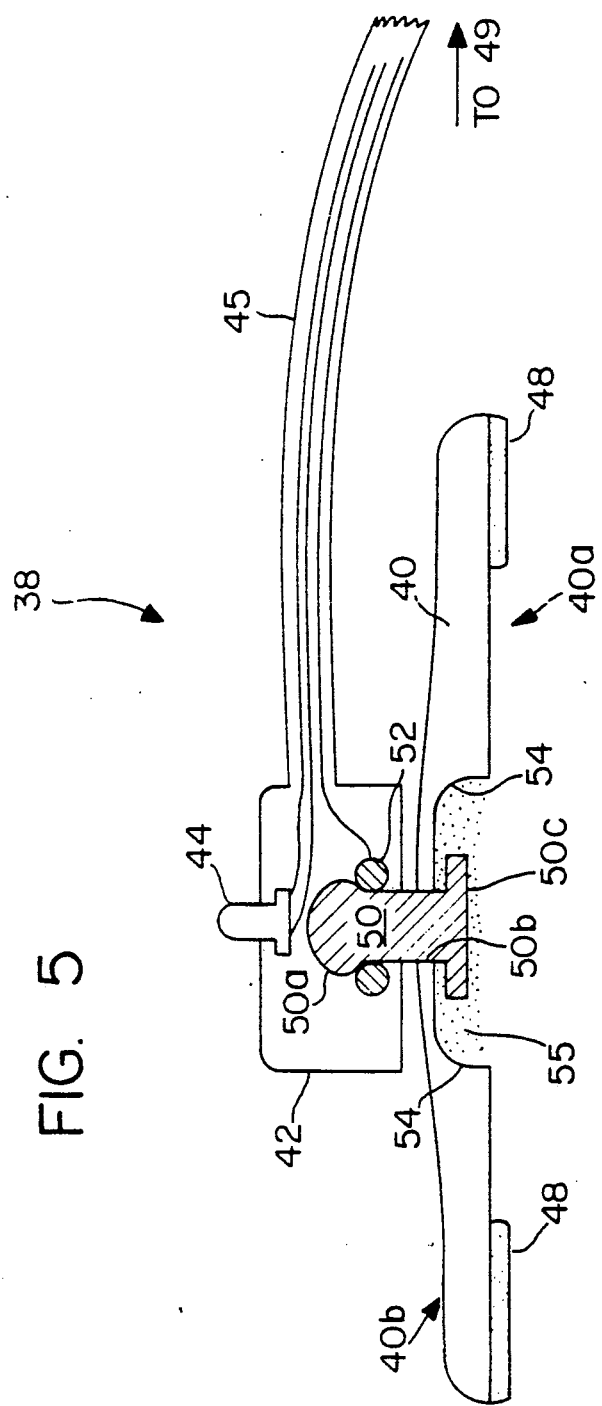
FIG. 5 is a schematic, cross-sectional view of the electrode pictured in FIG. 3.

FIG. 5 is a schematic, cross-sectional view of the electrode 38 pictured in FIG. 3. In the preferred embodiment of the invention, an LED 44 in anchored in the top central portion of snap connector 42. Wires from the LED 44 run into lead 45 that extend to ECG instrument 46 (not shown in FIG. 5). An adhesive 48 attached to pad 40 provides a means of securing the present invention to a patient. The electrode 38 comprises a metal post 50 embedded in the center of pad 40. The post 50 protrudes up from the insulative pad 40 through connector side 40b, which is the side opposite the side that touches the patient's skin. The post 50 has an upper rounded portion 50a shaped like a flattened or oblate spheroid. A generally cylindrical shank or middle portion 50b extends downward from the rounded top 50a to a lower portion 50c that is shaped like a flange and is contained within the body of pad 40. A spring contact 52 surrounds post 50 and provides an electrical coupling to one of the wires inside lead 46. The bottom portion 50c of the post 50 extends through and past a lower central surface 54 of pad 40 that is capable of holding a volume of conductive jelly 55. In the preferred embodiment of the present invention, the lower central surface 54 is shaped like a concave surface to promote the adhesion of the jelly to the electrode. The jelly 55 is commonly used to enhance the electrical continuity between electrodes and the epidermis.

Figure 6:
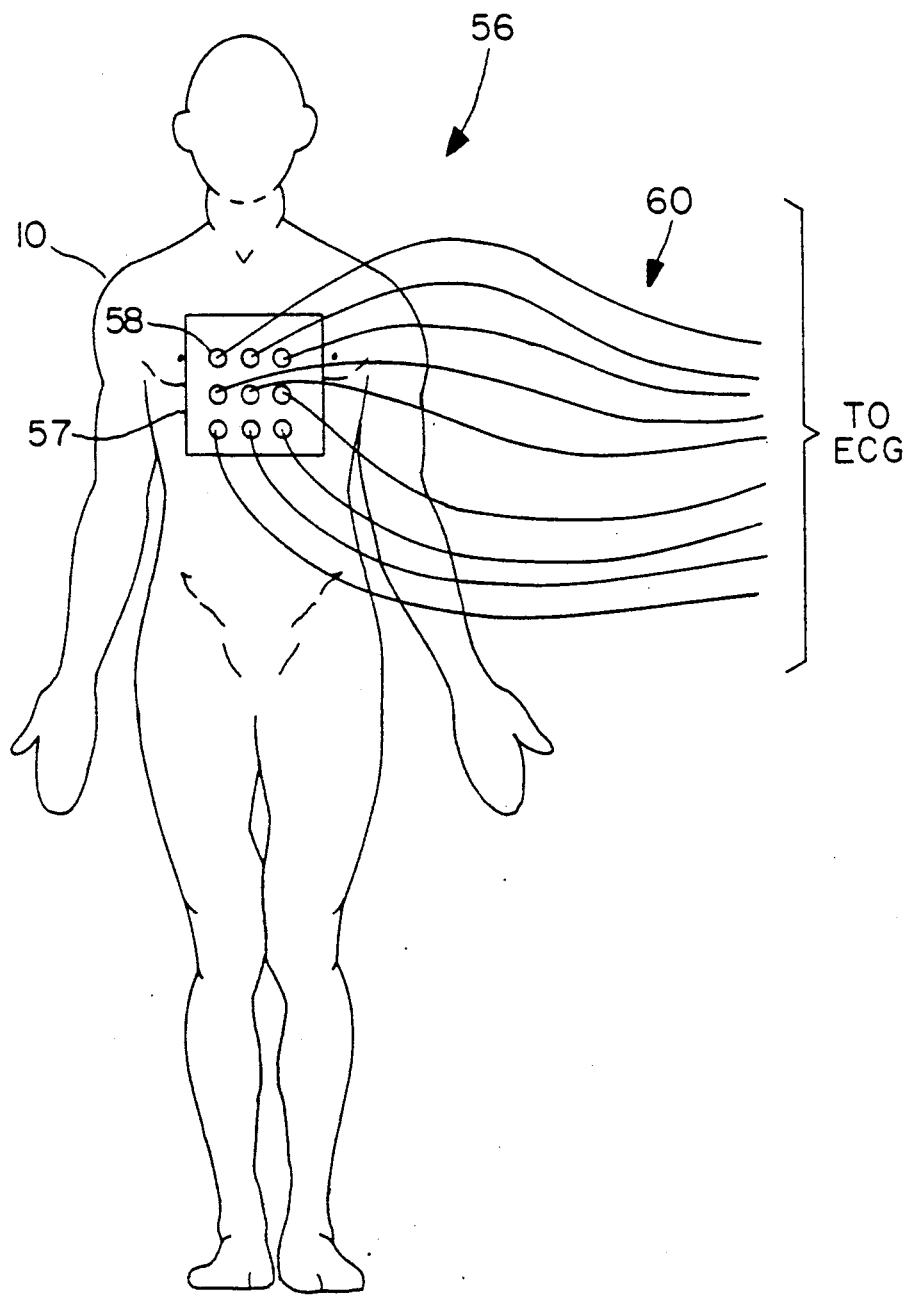
FIG. 6 is an illustration which shows a patient fitted with a multi-connector Intelligent ECG System array.

FIG. 6 is an illustration which shows a patient fitted with a multi-connector Intelligent ECG System array 56. The array includes a multi-connector ECG pad 57 which has a number of individual connection sites 58 that are each coupled to a set of leads 60. An alternative embodiment of the multi-lead array may employ a number of electrodes 38 and leads 60 without pad 57.

Figure 7:
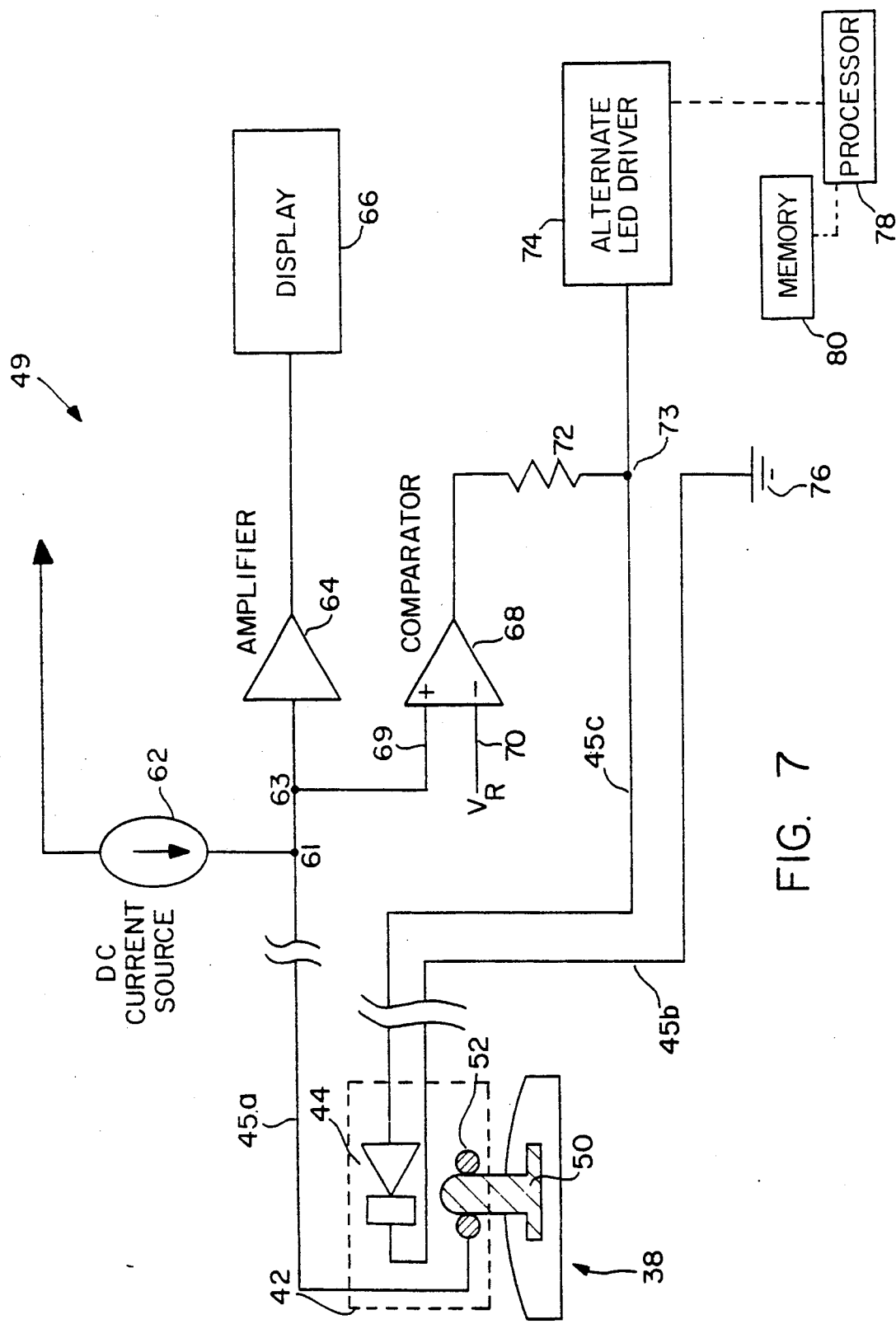
FIG. 7, 8, and 9 are schematic diagrams of the circuitry employed by the present invention.

FIG. 7 is a diagram that includes the sensor circuitry employed by the present invention. Electrode 38, which includes snap connector 42, LED 44, metal post 50, and spring contact 52, is shown with detector circuitry 49 in this schematic representation. Line 45a connects spring clip 52 to node 61, which is also connected to a current source 62 and node 63. An amplifier 63 and display 64 extend in series from node 63, which is also linked to the positive terminal 69 of a comparator 68. A reference voltage Vr is applied to the comparator's negative terminal 70. The output of the comparator 68 flows through a resistor 72 that is coupled to node 73, which is also connected to lead 45c from LED 44 and an alternate LED driver 74. The second lead 45b from the LED 44 is grounded at ground terminal 76. In the preferred embodiment, the detector 49 comprises the current source 62, comparator 68, and resistor 72 in the arrangement shown in FIG. 7.

When the electrode 38 is attached to a patient, wire 45a conducts the ECG signal from metal post 50 to amplifier 64. The amplified signal is then presented as a waveform on display 66. When the coupling between the electrode 38 and the patient is faulty or inadequate, the electrode impedance becomes relatively high compared to its nominal value while there is good electrical continuity between the electrode and the patient's skin. When this impedance rises, the small flow of current from source 62 causes the voltage at lead 45a (node 61) to rise above reference voltage Vr, which is applied at negative input terminal 70 of comparator 68. This change, in turn, causes the output of the comparator 68 to rise to a positive voltage which is capable of turning on LED 44. Resistor 72, which lies in series between comparator 68 and LED 44, serves to limit the current which can flow back to the LED 44 through leads 45b and 45c. Lead 45c, which is coupled to ground terminal 76, can also be conveniently employed as a shield for the leads that convey the ECG signal from electrode 38.

The LED 44 can also be driven by another signal such as a lead sequencer 74. If the multi-electrode embodiment shown in FIG. 6 is employed, the LEDs 44 can be illuminated sequentially to guide a technician to attach each electrode to the patient in the proper order and in the appropriate location. This operation can be accomplished using a driver 74 that contains a microprocessor 78 which is capable of storing a program in a memory 80 and then executing the stored program to help a technician perform a complex ECG procedure. The processor can also be configured to provide instructions for the user on display 66.

Figure 8:
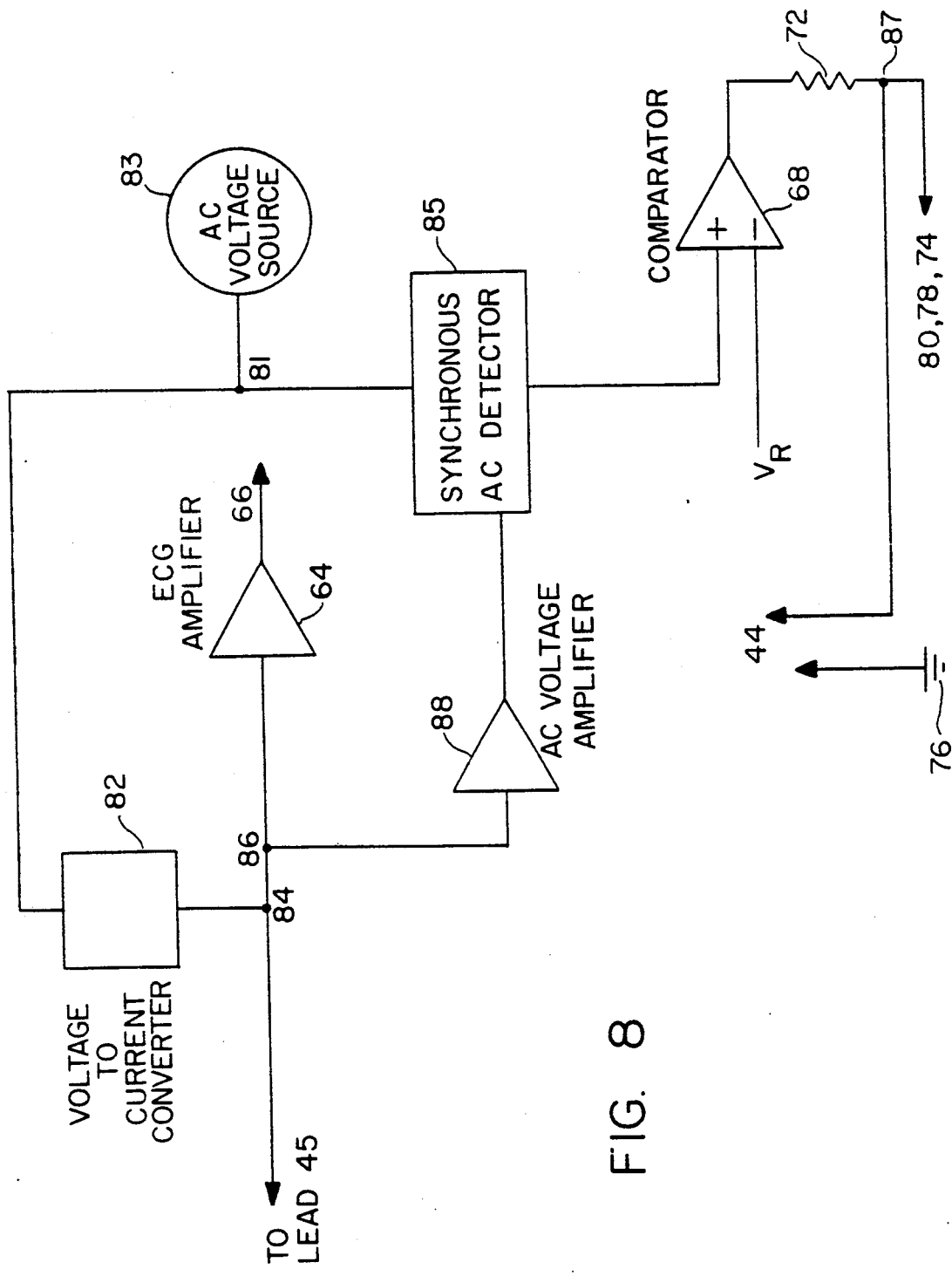

FIG. 8 presents an alternative circuit which may be employed to practice the present invention. Unlike the DC current source 62 provided in the hardware shown in FIG. 7, the configuration illustrated by FIG. 8 utilizes a voltage to current converter 82 and an AC voltage source 83. The voltage to current converter 82 may employ a single resistor or a single capacitor. Lead 45 from electrode 38 is connected to converter 82 at node 84, and both are coupled to ECG amplifier 64, display 66, and AC voltage amplifier 88 at node 86. An AC voltage source 83 is coupled to converter 82 at node 81. An AC voltage amplifier 88 feeds a signal to a synchronous AC detector 85, which, in turn, provides an output to comparator 68. The synchronous AC detector 85 is selected to provide a high signal-to-noise ration. In an alternative embodiment, a tuned detector may be substituted for the synchronous detector 85. Just as in FIG. 7, LED 44 draws current from comparator 68 through resistor 72. The hardware depicted in FIG. 8 may also include an alternate LED driver 74, a processor 78, and a memory 80 connected in series from node 87.

The AC converter 82 and AC voltage source 83 may be beneficially employed when the frequency chosen for the system is outside of the passband of the ECG amplifier 64. The electrode to skin impedance is then measured by sensing the AC voltage on lead 45, which is accomplished by placing an AC amplifier 88 and detector 85 in series between node 86 and comparator 68. One advantage that is gained by using a low radiofrequency AC signal of about 50 kHz is that the present invention is then also capable of measuring the impedance between two electrodes 38 as it changes slightly with the patient's respiration rate.

An alternative embodiment of the invention may utilize a sensor circuit which measures a change in capacitance between the patient 10 and the electrode 38 to determine when such a failure has occured.

Figure 9:
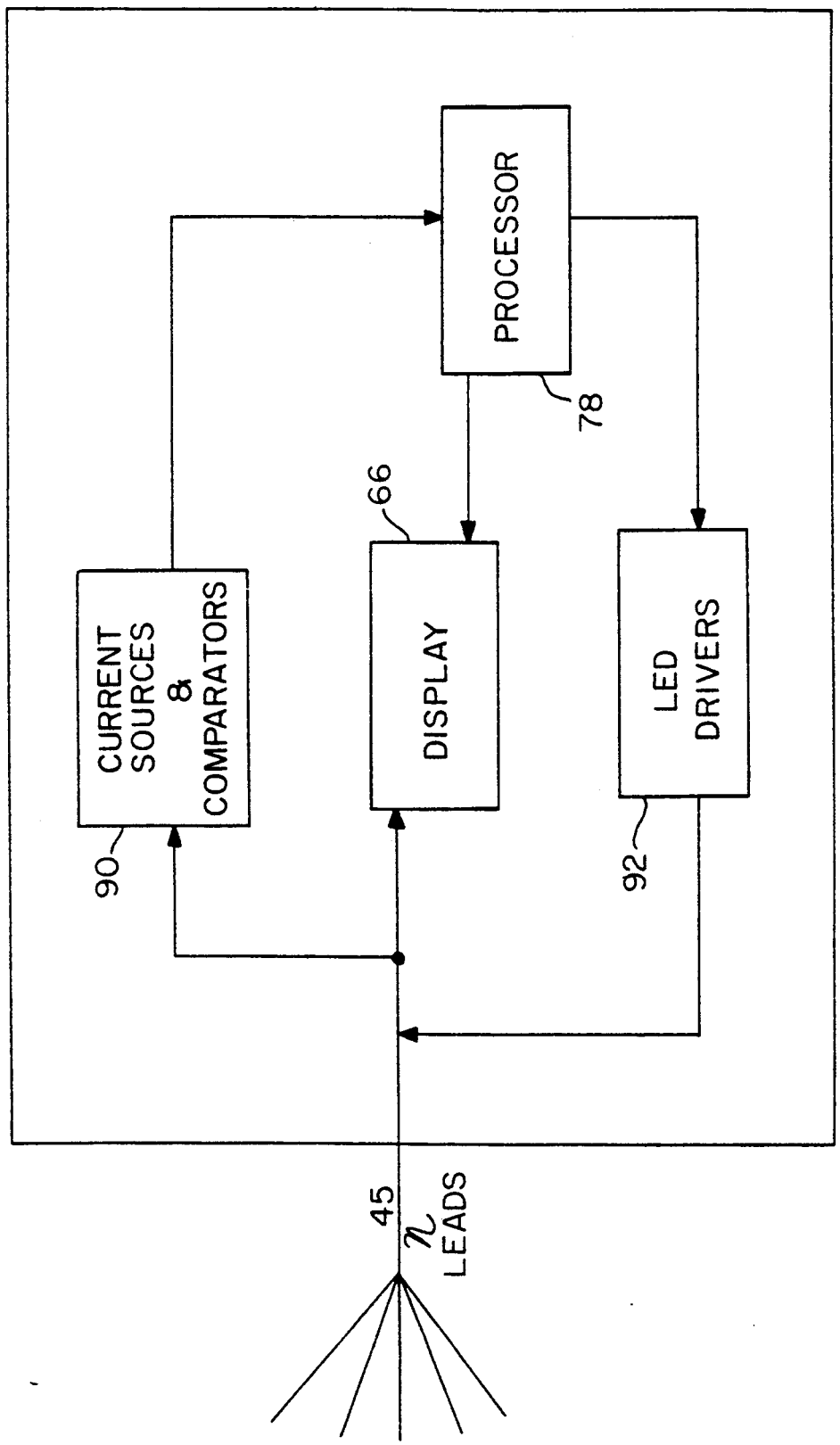

FIG. 9 is a schematic depiction of circuitry which may be used to practice the present invention. Comparator 68 may not necessary be employed to drive LED 44 directly, although such an arrangement would suffice and may lead to significant cost savings for the manufacturer. In another configuration, a large number of leads 45 may be coupled to current sources and comparators 90 and LED drivers 92 with a microprocessor 78 and a display 66 as shown in FIG. 9. When this circuitry senses a voltage level that is associated with a poorly attached electrode 38, processor 78 acts to turn on the LED 44 affixed to that deficiently attached electrode 38. The hardware shown in FIG. 9 could also be used to illuminate a number of LEDs 44 in a particular sequence to guide a technician through the task of placing a group of electrodes 38 in their proper locations on a patient. In this case, the comparators may be employed to signal that an adequate electrical contact has been established between the electrode and the subject's skin. Simultaneously, the processor 78 could be programmed to feed textual or diagrammatic instructions to display 66 to guide a technician as the LEDs on each electrode are activated in a predetermined order.

Although the present invention has been described in detail with reference to a particular preferred embodiment, persons possessing ordinary skill in the art to which this invention pertains will appreciate that various modifications and enhancements may be made without departing from the spirit and scope of the claims that follow.

LIST OF REFERENCE NUMERALS

FIG. 1
10 Patient
12 Connections to patient's skin
14 Leads
16 Electrocardiogram instrument
18 Display
FIG. 2
19 Conventional electrode
T Terminal side
C Contact side
20 Outer portion
22 Central portion
24 Terminal
26 Spring clip
27 Lead
28 Inner portion of contact side of electrode
30 Central conductive portion of contact side of electrode
31 Snap connector
32 Outer portion of snap connector
34 Conductive portion of snap connector
36 Recess in center of snap connector
FIGS. 3 and 4
38 Intelligent ECG System connector
40 Electrode
40a Contact side of electrode
40b Connector side of electrode
42 Electrode snap connector
44 LED
45 Lead
46 ECG Instrument
47 Display
FIG. 5
48 Adhesive
49 Detector circuit
50 Metal post
50a Upper portion
50b Middle portion
50c Lower portion
52 Spring contact fitted around post
54 Lower central conductive surface of pad
55 Conductive jelly
FIG. 6
56 Multi-connector Intelligent ECG System Array
57 Multi-connector Intelligent ECG System Array pad
58 Individual connection site
60 Multiple leads to ECG instrument
FIG. 7
61 Node
62 DC current source
63 Node
64 Amplifier
66 Display
68 Comparator
69 Positive input terminal of comparator
70 Negative input terminal of comparator
72 Current limiting resistor
73 Node
74 Alternate LED driver
76 Ground
78 Processor
80 Memory
FIG. 8
81 Node
82 Voltage to current converter
83 AC voltage source
84 Node
85 Synchronous AC detector
86 Node
87 Node
88 AC amplifier
FIG. 9
90 Current sources and comparators
92 LED drivers

What is claimed is:

1. An apparatus for automatically detecting a failure of a connection placed on a patient by activating an alarm on said patient where said failure occurs comprising:
 a conductive means for making an electrical connection to said patient;
 a coupling means for making an electrical connection to said conductive means; said coupling means having an end portion attached to said conductive means;
 a detector means coupled to said conductive means for sensing when said conductive means becomes partially detached from said patient; and
 an alarm means for indicating a failure when said detector means senses an inadequate connection between said conductive means and said patient; said alarm means being affixed to said end portion of said coupling means; said alarm means also being located generally next to said conductive means to precisely indicate the position of said failure.

2. An apparatus as claimed in claim 1, further comprising an insulative pad means for making an insulating connection to said conductive means; said insulative pad means having a lower central surface; said insulative pad means also having an adhesion means coupled to said conductive means for maintaining said conductive means in contact with said patient.

3. An apparatus as claimed in claim 2, in which said conductive means comprises
 a generally cylindrical metal post which protrudes up from said insulative pad means from said lower central surface of said pad means; said metal post including:
  an upper, generally oblate spheroid portion,
  a middle shank portion, and
  a lower flange portion; and
 a volume of conductive jelly held by contact with said lower central surface of said pad means; said lower flange portion of said post extending into said volume of conductive jelly.

4. An apparatus as claimed in claim 1, in which said detector means measures a change in resistance between said conductive means and said patient.

5. An apparatus as claimed in claim 1, in which said alarm means is a light.

6. An apparatus as claimed in claim 1, in which said alarm means is an LED.

7. An apparatus as claimed in claim 1, in which said alarm means is an audible alarm.

8. An Intelligent Electrocardiogram System comprising:

an insulative pad having a contact side and a connector side;
a generally cylindrical metal terminal having an upper portion, a middle portion, and a lower portion; said upper portion protruding from said connector side; said terminal extending through said pad to said contact side;
a volume of conductive jelly in contact with said lower portion of said terminal;
a spring contact located around said middle portion of said metal terminal;
a lead connected to said spring contact;
an adhesive located on said contact side of said pad for maintaining attachment to a patient;
a detector that measures a change in electrical impedance between said metal terminal and said patient; said detector including a DC current source, a comparator, and a current limiting resistor; said current source being connected to said terminal; said comparator being connected to said current source; said resistor being connected to said comparator;
a lamp which illuminates when said detector senses said change in electrical impedance; said lamp being connected to said comparator through said resistor;
an ECG amplifier coupled to said lead; and
an ECG display coupled to said ampliflier.

9. An Intelligent Electrocardiogram System comprising:
an insulative pad having a contact side and a connector side;
a generally cylindrical metal terminal having an upper portion, a middle portion, and a lower portion; said upper portion protruding from said connector side; said terminal extending through said pad to said contact side;
a volume of conductive jelly in contact with said lower portion of said terminal;
a spring contact located around said middle portion of said metal terminal;
a lead connected to said spring contact;
an adhesive located on said contact side of said pad for maintaining attachment to a patient;
an AC sensor circuit that measures a change in electrical impedance between said metal terminal and said patient; said AC sensor circuit including
a voltage to current converter,
an AC voltage source,
a synchronous AC detector,
an AC voltage amplifier,
a comparator, and
a current limiting resistor;
said converter being connected to said terminal; said AC voltage source being connected between said converter and said synchronous AC detector; said AC voltage amplifier being connected between said converter and said synchronous AC detector; said comparator being connected to said synchronous AC detector; said resistor being connected to said comparator;
a lamp which illuminates when said detector senses said change in electrical impedance; said lamp being connected to said comparator through said resistor;
an ECG amplifier coupled to said lead; and
an ECG display coupled to said amplifier.

* * * * *